(12) United States Patent
Williams et al.

(10) Patent No.: US 6,510,331 B1
(45) Date of Patent: Jan. 21, 2003

(54) SWITCHING DEVICE FOR MULTI-SENSOR ARRAY

(76) Inventors: Glenn Williams, 3633 Bayshore Blvd. NE., St. Petersburg, FL (US) 33703; Bill Williams, 3848 S. Rockbridge Rd., Stone Mountain, GA (US) 30087

( * ) Notice: Subject to any disclaimer, the term of this patent is extended or adjusted under 35 U.S.C. 154(b) by 61 days.

(21) Appl. No.: 09/586,925

(22) Filed: Jun. 5, 2000

(51) Int. Cl.[7] ................................................ A61B 5/00
(52) U.S. Cl. ...................................... 600/323; 600/340
(58) Field of Search ................. 600/309–311, 315–326, 600/336, 340, 344; 359/39–40

(56) References Cited

U.S. PATENT DOCUMENTS

| | | | |
|---|---|---|---|
| 5,282,464 A | * 2/1994 | Brain | 128/207.15 |
| 5,339,810 A | 8/1994 | Ivers et al. | |
| 5,353,793 A | * 10/1994 | Bornn | 600/386 |
| 5,627,531 A | * 5/1997 | Posso et al. | 341/22 |
| 5,776,059 A | 7/1998 | Kaestle et al. | |
| 5,842,982 A | 12/1998 | Mannheimer | |
| 5,938,593 A | * 8/1999 | Ouellette | 600/300 |
| 5,978,691 A | * 11/1999 | Mills | 600/334 |
| 6,334,065 B1 | * 12/2001 | Al-Ali et al. | 600/323 |

FOREIGN PATENT DOCUMENTS

| | | | |
|---|---|---|---|
| EP | 0290278 | * | 6/1988 |
| JP | 60-232132 | * | 5/1984 |

* cited by examiner

Primary Examiner—Eric F. Winakur
Assistant Examiner—Matthew Kremer
(74) Attorney, Agent, or Firm—Larson & Larson, P.A.; James E. Larson

(57) ABSTRACT

A switching device is interposed between a conventional oximeter and a plurality of conventional photosensors. The photosensors are located on different extremities of the body. The switching device may be operated in the manual mode or an automatic mode. In the manual mode each different photosensor may be individually selected to provide the input signal to the oximeter. In the automatic mode, the switching device scans the incoming signals from the different photosensors and forwards the best, strongest or least distorted signal to the oximeter. The device prevents the loss of oximetery information due to interrupted blood flow in a particular part of the body or the failure of a sensor.

9 Claims, 2 Drawing Sheets

SWITCHING DEVICE FOR MULTI-SENSOR ARRAY

FIELD OF THE INVENTION

This invention relates to a switching device for manually or automatically selecting a certain signal among a plurality of signals generated by a plurality of sensors. Specifically, this invention relates to oximeters used to generate a representation of oxygen saturation levels in arterial blood flow in a patient.

BACKGROUND OF THE INVENTION

The use of oximeters is conventional in the medical field. Oximeters are used in the operating room (OR) and the intensive care unit (ICU), as well as in other applications, to provide information regarding the oxygen level in a patient's blood.

In normal use, the oximeter is made up of an powered analyzer section electrically connected to a sensor. In a conventional pulse oximeter, the sensor has a light emitting diode (LED) mounted on one side of the patient's extremity, such as a finger, and a phototransistor receptor mounted on the other side. The LED sends pulses of light, in a known wavelength, into the finger. The receptor receives the light that is transmitted through the tissue and converts it to an electrical signal. There are also conventional sensors that generate a signal on the reflected light rather than transmitted light. In any event, the electrical signal is returned to the analyzer section where it is converted to a read-out which may be graphical or numerical and may be printed or displayed on a screen (CRT).

It is especially important to maintain a sterile field in the OR and the ICU. The equipment used in these locations should be sterile, also. The oxygen level in the patient's blood is constantly monitored to determine the patient's well being in both these settings. In certain situations in the OR, during surgery, blood flow in a particular part of the body may be interrupted or shunted into other fields. Such an event may cause the interruption of the oximeter readings, if the sensor is located on an extremity in the affected part of the body. To immediately reestablish this vital information, the sterile field may be invaded to place another sensor on the body or to move the affected sensor to another suitable location on the patient.

This situation may also occur in the ICU. Also, in the ICU the patient may cause the sensor to become dislodged through body movement. Of course, there are other mechanical reasons that a sensor may malfunction and require replacement.

This important information concerning the patient's oxygen blood level is lost during the period of time required to position a new oximeter and hook up another sensor.

Thus, what is needed in the art is an apparatus that will provide continuous blood oxygenation readings without disturbing the patient or the sterile field when blood flow to a particular part of the body is interrupted or a sensor fails.

DESCRIPTION OF THE PRIOR ART

Mannheimer, U.S. Pat. No. 5,842,982, discloses a neonatal pulse oximeter sensor for application to the foot of a baby.

Ivers et al, U.S. Pat. No. 5,339,810 and Kaestle et al, U.S. Pat. No. 5,776,059 show pulse oximetry sensors for the finger of a patient.

Sensors may be placed on any part of the anatomy where there is a good blood flow that can be impinged by a light source, including the fingers, toes, earlobes, and nares, among others.

The conventional oximeter or the analyzer section, per se, has software, based on the Lambert-Beer equations, which converts the incoming signal from the sensor to a usable representation. The representation may take any desired form, both digital and analog.

SUMMARY OF THE INVENTION

A switching device interposed between an oximeter and a plurality of photosensors located on various body extremities. The switching device may be operated in a manual mode wherein each photosensor may be individually selected to provide the input signal to the oximeter. The switching device may also be operated in an automatic mode wherein the switching device scans the incoming signals from the different photosensors and forwards the best, strongest or least distorted signal to the oximeter. The device prevents the loss of oximetery information due to interrupted blood flow in a particular part of the body or the failure of a sensor.

It is an objective of this invention to provide an oximeter having an array of sensors connected to different parts of the patient's body to continuously generate blood oxygenation information in the event blood supply is interrupted in a particular part of the body or a sensor malfunctions.

It is another objective of this invention to provide a switching device interposed between the array of sensors and the analyzer section for selection of a particular incoming signal from one of the sensors.

It is yet another objective of this invention to provide the switching device with a manual mode and an automatic mode of operation.

Other objectives and advantages of this invention will become apparent from the following description taken in conjunction with the accompanying drawings wherein are set forth, by way of illustration and example, certain embodiments of this invention. The switching device of this invention need not be restricted to pulsoximetry but can be used in other general measuring systems in which plural sensors are arrayed with a single display mechanism. The drawings constitute a part of this specification and include exemplary embodiments of the present invention and illustrate various objects and features thereof.

DETAILED DESCRIPTION OF THE INVENTION

Figure 1:
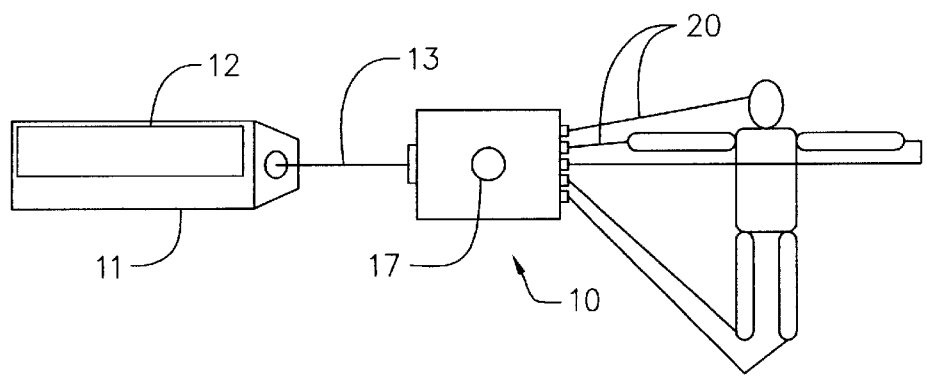
FIG. 1 shows a block diagram of the switching device and an oximeter/analyzer section.

The switching device 10 is shown operatively connected to an oximeter/analyzer section 11 by output cable 13, in FIG. 1. The oximeter/analyzer section 11 and display 12 are well known in the art and operate to alternately energize the sensors 30 (shown in FIG. 3) and to calculate and display the oximetry value from the light detected at each wavelength by a photoreceptor 23.

The switching device 10 is illustrated in the general form of a rectangular housing 14, though the exact shape is of no moment. On one surface of the housing 14 there is a rotary selector knob 17. The selector knob 17 may be manually placed in any one of several positions as indicated about the circumference of the knob, by rotating the knob. As seen in FIG. 1, sensor position 19, labeled RL, is selected. The alphabetical designations 15 and 19 are related to the pictograph 21 shown in FIG. 2. The RL refers to, right leg, though the photosensor may be attached to a toe or the heel of the right foot. This general description is true of the other designations as well.

As shown in FIG. 1, the input connections 20 each go to an individual sensor located on a part of the body as labeled on the face of the box 14. In addition to the anatomical label, each connection includes a light 16 which illuminates to indicate an active sensor.

There are situations, as in the case of reattachment of extremities, in which the array of sensors may be placed on the digits of the same hand or foot. In this manner, the blood flow to the reattached hand or foot could be monitored in each finger or toe of that extremity merely by switching the knob to the different positions.

When the selector knob 17 is placed on the AUTO designation 18, the switching device will select the best incoming signal for forwarding to the analyzer section. The best signal may be the strongest or the least distorted sensor signal. The switching device may include a memory circuit for comparison purposes or there may be a gain set above the lowest acceptable signal. The sensor signals are scanned and the first or most acceptable signal is forwarded to the analyzer section. If a signal is lost, the switching device immediately selects another sensor.

Figure 2:
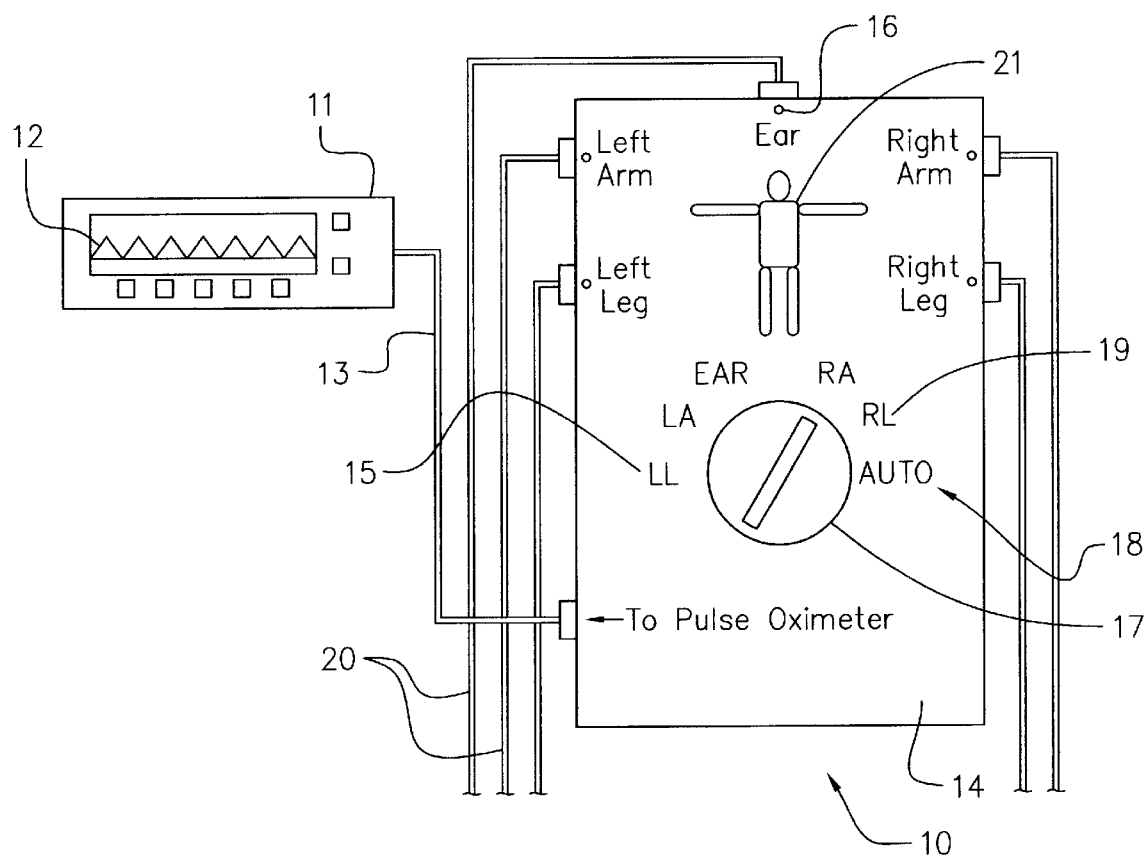
FIG. 2 shows a block diagram of the switching device with a pictograph.

FIG. 2 shows the general organization of the oximeter 11 and switching device housing 14. The switching device housing 14 has a pictograph 21 on one surface illustrating the location of various sensors on the patient's body. The leads 20 exit the box 14 as indicated by the pictograph. The pictograph 21 can be substituted for or in addition to the alphabetical labels shown in FIG. 1. The pictograph may be on another face of the box 14 or may be on the same face with the alphabetical labels.

Figure 3:
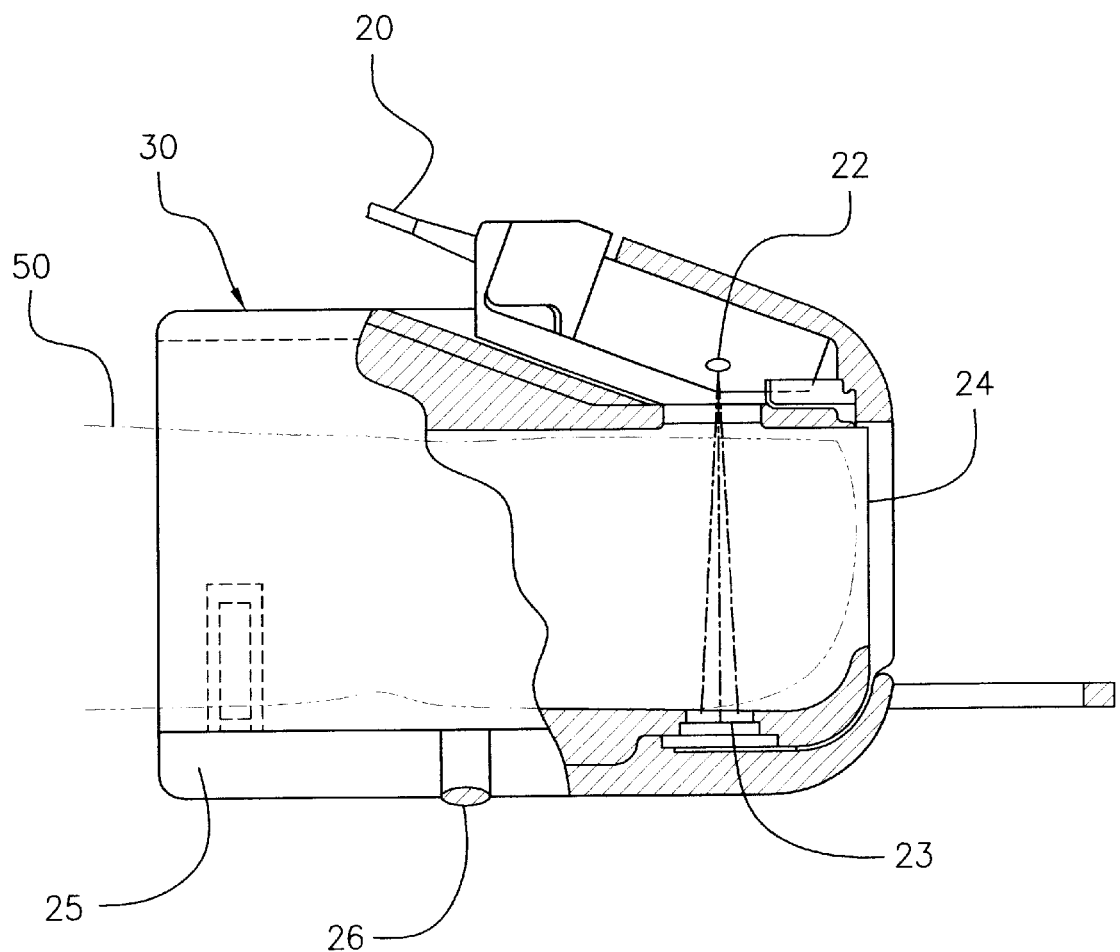
FIG. 3 shows a cross section of a photosensor.

FIG. 3 illustrates a conventional photosensor used in pulse oximetry. The sensor 30 has a casing 25 into which a patient's extremity is inserted. In this illustration the casing 25 is mounted on the patient's finger 50 and secured by a resilient fastener 26, such as a rubber band. The connection 20 carries power and the return signal. The pulse LED 22 is energized sending a burst of light into the finger 50. The photoreceptor 23 picks up the transmitted light and sends a return signal through line 24 and line 20 back to the switching device. As shown in FIG. 3, line 24 and line 20 are connected through a plug-in on the casing 25.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A method of providing continuous blood oxygenation readings, said method comprising the steps of:

a) providing an oximeter which produces said readings, said oximeter having a plurality of sensors, each sensor operating at the same infrared wavelength and adapted to be temporarily connected to extremities of a body;

b) mounting each of said sensors on a different extremity;

c) connecting a switching device to said oximeter and said plurality of sensors, said switching device having a selector, said selector having multiple positions, each of said positions energizing one of said plurality of sensors at a time and conveying the return signal from the energized sensor to said oximeter;

d) selecting a particular position and energizing said sensor by operation of said selector; and e) producing a blood oxygenation reading from each selected sensor so that loss of oximetry information caused by interrupted blood flow in one sensed part of the body or failure of a sensor will not prevent the continuous flow of blood oxygenation readings.

2. A method of providing continuous blood oxygenation readings of claim 1 including the step of manually selecting a particular sensor using said selector.

3. A method of providing continuous blood oxygenation readings of claim 1 including providing said selector with a position in which said switching device scans each of said return signals of said plurality of sensors, automatically selects the best return signal, and conveys said selected signal to said oximeter.

4. A method of providing continuous blood oxygenation readings of claim 3 including the step of manually selecting a particular position.

5. A switching device for a blood oximeter having plural sensors, each operating at the same infrared wavelength and each sensor adapted to provide a same output, said switching device comprising a housing, said housing including an output connection adapted for communication to said oximeter and a plurality of input connections each adapted for communication with one of said plural sensors connected at a body extremity site, a selector carried by said housing for selectively connecting a particular input connection to said output connection, and a plurality of indicators on said housing for showing which of said input connections is active so that loss of oximetry information caused by interrupted blood flow at one sensor or failure of one sensor will not prevent the continuous flow of blood oxygenation readings.

6. A switching device of claim 5 wherein said selector is rotary and said plurality of indicators are mounted on said housing about the circumference of said rotary selector.

7. A switching device of claim 5 wherein said housing includes means for scanning each of said input connections and automatically selecting a particular input connection for communication with said oximeter.

8. A switching device of claim 7 wherein said input connections carry a signal and said means automatically selects the best signal for communication with said oximeter.

9. A switching device of claim 7 wherein said means may be selectively engaged by said selector and said plurality of indicators includes an indicator for showing that said means is active.

* * * * *